US012733952B2

(12) United States Patent
Massimini et al.

(10) Patent No.: US 12,733,952 B2
(45) Date of Patent: Sep. 15, 2026

(54) ATHERECTOMY SYSTEM ADAPTED TO ENABLE RETROGRADE ABLATION

(71) Applicant: Boston Scientific Scimed, Inc., Maple Grove, MN (US)

(72) Inventors: Daniel Frank Massimini, Brooklyn Park, MN (US); Michael Kaland, Minneapolis, MN (US); Corydon Carlson, Stillwater, MN (US); Jarrod Kenneth Neuharth, Minneapolis, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1047 days.

(21) Appl. No.: 17/894,071

(22) Filed: Aug. 23, 2022

(65) Prior Publication Data

US 2023/0218314 A1 Jul. 13, 2023

Related U.S. Application Data

(60) Provisional application No. 63/297,953, filed on Jan. 10, 2022.

(51) Int. Cl.

| | |
|---|---|
| ***A61B 17/3207*** | (2006.01) |
| ***A61B 17/22*** | (2006.01) |
| ***A61M 25/01*** | (2006.01) |

(52) U.S. Cl.

CPC . *A61B 17/320758* (2013.01); *A61M 25/0147* (2013.01); *A61B 2017/22038* (2013.01)

(58) Field of Classification Search

CPC . A61B 17/320758; A61B 2017/22038; A61M 25/0147

(Continued)

(56) References Cited

U.S. PATENT DOCUMENTS

| | | | |
|---|---|---|---|
| 2,088,654 | A | 8/1937 | Hull |
| 3,913,196 | A | 10/1975 | Maday |

(Continued)

FOREIGN PATENT DOCUMENTS

| | | | |
|---|---|---|---|
| CA | 2682488 | A1 | 10/2008 |
| DE | 202005022017 | U1 | 5/2012 |

(Continued)

OTHER PUBLICATIONS

International Search Report and Written Opinion dated Oct. 17, 2022 for International Application No. PCT/US2022/041260.

(Continued)

*Primary Examiner* — Kankindi Rwego
(74) *Attorney, Agent, or Firm* — Seager, Tufte & Wickhem, LLP

(57) ABSTRACT

An atherectomy system is adapted for both anterograde ablation and retrograde ablation, and includes a drive coil and an atherectomy tool coupled to the drive coil, the atherectomy tool including a distal region adapted for anterograde ablation and a proximal region adapted for retrograde ablation. A proximal handle includes an actuation member adapted to be movable in a first direction to urge the atherectomy tool in an anterograde ablation direction and to be movable in a second direction to urge the atherectomy tool in a retrograde ablation direction. The atherectomy system is adapted such that the actuation member provides a similar feedback to a user regardless of whether the atherectomy tool is ablating in the anterograde ablation direction or in the retrograde ablation direction.

17 Claims, 11 Drawing Sheets

(58) Field of Classification Search
USPC .......................................................... 606/159
See application file for complete search history.

(56) References Cited

U.S. PATENT DOCUMENTS 4,395,167 A 7/1983 Maternus
4,507,028 A 3/1985 Matsushita
4,679,557 A 7/1987 Opie et al.
5,116,350 A 5/1992 Stevens
5,287,858 A 2/1994 Hammerslag et al.
5,308,354 A 5/1994 Zacca et al.
5,314,407 A 5/1994 Auth et al.
5,417,703 A 5/1995 Brown et al.
5,478,344 A 12/1995 Stone et al.
5,501,694 A 3/1996 Ressemann et al.
5,540,707 A 7/1996 Ressemann et al.
5,563,481 A 10/1996 Krause
5,572,609 A 11/1996 Li
5,626,444 A 5/1997 Campian
5,632,755 A 5/1997 Nordgren et al.
5,674,235 A 10/1997 Parisi
5,681,336 A 10/1997 Clement et al.
5,709,661 A 1/1998 Van Egmond et al.
5,766,192 A 6/1998 Zacca
5,779,722 A 7/1998 Shturman et al.
5,823,990 A 10/1998 Henley
5,827,323 A 10/1998 Klieman et al.
5,836,868 A 11/1998 Ressemann et al.
5,899,915 A 5/1999 Saadat
5,913,867 A 6/1999 Dion
6,015,420 A 1/2000 Wulfman et al.
6,017,354 A 1/2000 Culp et al.
6,086,608 A 7/2000 Ek et al.
6,102,926 A 8/2000 Tartaglia et al.
6,106,301 A 8/2000 Merril
6,113,615 A 9/2000 Wulfman
6,120,515 A 9/2000 Rogers et al.
6,126,667 A 10/2000 Barry et al.
6,139,510 A 10/2000 Palermo
6,149,663 A 11/2000 Strandberg et al.
6,171,312 B1 1/2001 Beaty
6,200,329 B1 3/2001 Fung et al.
6,212,300 B1 4/2001 Rengakuji
6,234,725 B1 5/2001 Campian
6,270,509 B1 8/2001 Barry et al.
6,312,438 B1 11/2001 Adams
6,494,888 B1 12/2002 Laufer et al.
6,500,186 B2 12/2002 Lafontaine et al.
6,503,227 B1 1/2003 Guo et al.
6,503,261 B1 1/2003 Bruneau et al.
6,506,196 B1 1/2003 Laufer
6,554,845 B1 4/2003 Fleenor et al.
6,569,085 B2 5/2003 Kortenbach et al.
6,579,298 B1 6/2003 Peskin et al.
6,626,917 B1 9/2003 Craig
6,632,230 B2 10/2003 Barry
6,663,639 B1 12/2003 Laufer et al.
6,719,763 B2 4/2004 Chung et al.
6,740,030 B2 5/2004 Martone et al.
6,746,457 B2 6/2004 Dana et al.
6,755,843 B2 6/2004 Chung et al.
6,773,441 B1 8/2004 Laufer et al.
6,808,491 B2 10/2004 Kortenbach et al.
6,818,001 B2 11/2004 Wulfman et al.
6,821,285 B2 11/2004 Laufer et al.
6,835,200 B2 12/2004 Laufer et al.
6,908,427 B2 6/2005 Fleener et al.
6,997,931 B2 2/2006 Sauer et al.
7,056,284 B2 6/2006 Martone et al.
7,063,710 B2 6/2006 Takamoto et al.
7,063,715 B2 6/2006 Onuki et al.
7,094,246 B2 8/2006 Anderson et al.
7,144,401 B2 12/2006 Yamamoto et al.
7,147,646 B2 12/2006 Dana et al.
7,153,314 B2 12/2006 Laufer et al.
7,220,266 B2 5/2007 Gambale
7,232,445 B2 6/2007 Kortenbach et al.
7,235,086 B2 6/2007 Sauer et al.
7,285,130 B2 10/2007 Austin
7,326,221 B2 2/2008 Sakamoto et al.
7,344,545 B2 3/2008 Takemoto et al.
7,347,863 B2 3/2008 Rothe et al.
7,361,180 B2 4/2008 Saadat et al.
7,530,985 B2 5/2009 Takemoto et al.
7,601,161 B1 10/2009 Nobles et al.
7,618,425 B2 11/2009 Yamamoto et al.
7,713,277 B2 5/2010 Laufer et al.
7,722,633 B2 5/2010 Laufer et al.
7,727,246 B2 6/2010 Sixto, Jr. et al.
7,736,373 B2 6/2010 Laufer et al.
7,776,057 B2 8/2010 Laufer et al.
7,776,066 B2 8/2010 Onuki et al.
7,842,051 B2 11/2010 Dana et al.
7,846,180 B2 12/2010 Cerier
7,857,823 B2 12/2010 Laufer et al.
7,896,893 B2 3/2011 Laufer et al.
7,918,867 B2 4/2011 Dana et al.
7,951,157 B2 5/2011 Gambale
7,992,571 B2 8/2011 Gross et al.
7,993,368 B2 8/2011 Gambale et al.
8,016,840 B2 9/2011 Takemoto et al.
8,021,376 B2 9/2011 Takemoto et al.
8,057,494 B2 11/2011 Laufer et al.
8,062,314 B2 11/2011 Sixto, Jr. et al.
8,066,721 B2 11/2011 Kortenbach et al.
8,087,856 B2 1/2012 Reed
8,105,355 B2 1/2012 Page et al.
8,211,123 B2 7/2012 Gross et al.
8,216,253 B2 7/2012 Saadat et al.
8,226,667 B2 7/2012 Viola et al.
8,277,468 B2 10/2012 Laufer et al.
8,287,554 B2 10/2012 Cerier et al.
8,287,556 B2 10/2012 Gilkey et al.
8,308,765 B2 11/2012 Saadat et al.
8,313,496 B2 11/2012 Sauer et al.
8,361,089 B2 1/2013 Chu
8,388,632 B2 3/2013 Gambale
8,425,555 B2 4/2013 Page et al.
8,454,631 B2 6/2013 Viola et al.
8,480,691 B2 7/2013 Dana et al.
8,540,735 B2 9/2013 Mitelberg et al.
8,551,120 B2 10/2013 Gambale
8,556,914 B2 10/2013 Vrba
8,585,720 B2 11/2013 Gross et al.
8,603,123 B2 12/2013 Todd
8,632,553 B2 1/2014 Sakamoto et al.
8,679,136 B2 3/2014 Mitelberg
8,709,022 B2 4/2014 Stone et al.
8,764,771 B2 7/2014 Chu
8,882,785 B2 11/2014 Dicesare et al.
8,926,634 B2 1/2015 Rothe et al.
8,992,570 B2 3/2015 Gambale et al.
9,011,466 B2 4/2015 Overes et al.
9,050,126 B2 6/2015 Rivers et al.
9,050,127 B2 6/2015 Bonnette et al.
9,089,325 B2 7/2015 Mitelberg et al.
9,125,646 B2 9/2015 Woodard, Jr. et al.
9,198,562 B2 12/2015 Mitelberg et al.
9,232,957 B2 1/2016 Adams
9,320,515 B2 4/2016 Dana et al.
9,474,536 B2 10/2016 Carrison et al.
9,486,126 B2 11/2016 West et al.
9,504,465 B2 11/2016 Chu
9,510,817 B2 12/2016 Saadat et al.
9,526,519 B2 12/2016 Kessler et al.
9,549,728 B2 1/2017 Chu
9,750,494 B2 9/2017 Gross et al.
9,788,831 B2 10/2017 Mitelberg
9,844,366 B2 12/2017 Woodard, Jr. et al.
9,867,610 B2 1/2018 Mitelberg et al.
9,931,488 B2 4/2018 Bunch et al.
10,045,871 B2 8/2018 Saadat et al.
10,052,122 B2 8/2018 Higgins et al.
10,130,437 B2 11/2018 Lee et al.

(56) References Cited

U.S. PATENT DOCUMENTS 10,143,463 B2 12/2018 Dana et al.
10,194,902 B2 2/2019 Nobles et al.
10,335,142 B2 7/2019 Raybin et al.
10,722,250 B2 7/2020 Tasci et al.
10,736,628 B2 8/2020 Yates et al.
10,960,178 B2 3/2021 Savastano et al.
11,304,723 B1 * 4/2022 To .................. A61B 17/320725
2001/0004700 A1 6/2001 Honeycutt et al.
2001/0037121 A1 11/2001 McGuckin, Jr. et al.
2002/0007190 A1 1/2002 Wulfman et al.
2002/0058956 A1 5/2002 Honeycutt et al.
2002/0107530 A1 8/2002 Sauer et al.
2002/0151917 A1 10/2002 Barry
2002/0161384 A1 10/2002 Wulfman et al.
2003/0093103 A1 5/2003 Malackowski et al.
2003/0204205 A1 10/2003 Sauer et al.
2004/0002699 A1 1/2004 Ryan et al.
2004/0068270 A1 4/2004 Alfred, III
2004/0138706 A1 7/2004 Abrams et al.
2004/0186368 A1 9/2004 Ramzipoor et al.
2005/0004579 A1 1/2005 Schneider et al.
2005/0015021 A1 1/2005 Shiber
2005/0033319 A1 2/2005 Gambale et al.
2005/0240146 A1 10/2005 Nash et al.
2005/0250985 A1 11/2005 Saadat et al.
2006/0074405 A1 4/2006 Malackowski et al.
2006/0074442 A1 4/2006 Noriega et al.
2006/0142775 A1 6/2006 Heneberry et al.
2006/0282094 A1 12/2006 Stokes et al.
2007/0093841 A1 4/2007 Hoogland
2007/0239140 A1 10/2007 Chechelski et al.
2007/0270908 A1 11/2007 Stokes et al.
2008/0039823 A1 2/2008 Shimogami et al.
2008/0086148 A1 4/2008 Baker et al.
2008/0097499 A1 4/2008 Nash et al.
2008/0146965 A1 6/2008 Privitera et al.
2009/0024085 A1 1/2009 To et al.
2009/0069829 A1 3/2009 Shturman
2009/0124975 A1 5/2009 Oliver et al.
2009/0177031 A1 7/2009 Surti et al.
2010/0121361 A1 * 5/2010 Plowe ............ A61B 17/320758 29/446
2010/0125276 A1 5/2010 Palermo
2010/0137681 A1 6/2010 Ewers et al.
2010/0198006 A1 8/2010 Greenburg et al.
2010/0312263 A1 12/2010 Moberg et al.
2011/0077673 A1 3/2011 Grubac et al.
2011/0213391 A1 9/2011 Rivers et al.
2011/0251554 A1 10/2011 Romoscanu
2011/0306995 A1 12/2011 Moberg
2012/0053606 A1 3/2012 Schmitz et al.
2012/0095461 A1 4/2012 Herscher et al.
2012/0130410 A1 5/2012 Tal et al.
2012/0136348 A1 5/2012 Condie et al.
2012/0158023 A1 6/2012 Mitelberg et al.
2012/0172963 A1 7/2012 Ryan et al.
2012/0179167 A1 7/2012 Wenderow et al.
2012/0185031 A1 7/2012 Ryan et al.
2012/0209176 A1 8/2012 Anderson
2012/0271327 A1 10/2012 West et al.
2013/0006248 A1 1/2013 Ellis
2013/0079763 A1 3/2013 Heckel et al.
2013/0096581 A1 4/2013 Gilkey et al.
2013/0103062 A1 4/2013 To et al.
2013/0253552 A1 9/2013 Schoenle et al.
2013/0274657 A1 10/2013 Zirps et al.
2013/0304093 A1 11/2013 Serina et al.
2014/0100574 A1 4/2014 Bono et al.
2014/0128668 A1 5/2014 Cox et al.
2014/0148835 A1 5/2014 Schmitz et al.
2014/0212457 A1 7/2014 Rifai
2014/0222042 A1 8/2014 Kessler et al.
2014/0249554 A1 9/2014 To et al.
2014/0261453 A1 9/2014 Carlson
2014/0277014 A1 9/2014 Higgins et al.
2014/0316447 A1 10/2014 Ellering et al.
2014/0316448 A1 10/2014 Higgins
2014/0316451 A1 10/2014 Higgins et al.
2014/0324052 A1 10/2014 Carrison et al.
2015/0011834 A1 1/2015 Ayala et al.
2015/0073448 A1 3/2015 Rydberg
2015/0125807 A1 5/2015 Shipley
2015/0126983 A1 5/2015 Alvarado et al.
2015/0164540 A1 6/2015 Higgins et al.
2015/0173776 A1 6/2015 Burke et al.
2015/0173838 A1 6/2015 Murphy et al.
2015/0201956 A1 7/2015 Higgins et al.
2015/0216554 A1 8/2015 Kessler et al.
2015/0327880 A1 11/2015 Wasicek et al.
2015/0335348 A1 11/2015 Cohen et al.
2016/0022307 A1 1/2016 Wasdyke et al.
2016/0045197 A1 2/2016 Mitelberg et al.
2016/0157886 A1 6/2016 WasDyke et al.
2016/0235434 A1 8/2016 Smith et al.
2016/0235441 A1 8/2016 Parkin
2016/0287284 A1 10/2016 Smith et al.
2016/0346003 A1 12/2016 Grothe et al.
2016/0354107 A1 12/2016 Nakano et al.
2017/0086817 A1 3/2017 Mitelberg
2017/0086818 A1 3/2017 Mitelberg
2017/0181760 A1 6/2017 Look et al.
2017/0189123 A1 7/2017 Govari et al.
2017/0273698 A1 9/2017 McGuckin, Jr. et al.
2017/0296200 A1 10/2017 Singer et al.
2018/0042602 A1 2/2018 Mitelberg et al.
2018/0042603 A1 2/2018 Mitelberg et al.
2018/0153381 A1 6/2018 Wei et al.
2018/0183179 A1 6/2018 Byrd et al.
2018/0193056 A1 7/2018 Colyer et al.
2018/0235604 A1 8/2018 Comee et al.
2018/0242998 A1 8/2018 Dhandhusaria et al.
2019/0142526 A1 5/2019 Hendrick et al.
2019/0175211 A1 6/2019 Carlson et al.
2019/0262032 A1 8/2019 Carlson et al.
2019/0262034 A1 8/2019 Spangler et al.
2020/0022764 A1 1/2020 Flexman et al.
2020/0060718 A1 2/2020 Patel et al.
2020/0069324 A1 3/2020 Deepa
2020/0229844 A1 7/2020 Rawson et al.
2020/0246029 A1 8/2020 Singleton et al.
2020/0315654 A1 10/2020 Patel et al.
2020/0345981 A1 11/2020 Garrison et al.
2021/0045770 A1 2/2021 Savastano et al.
2021/0077143 A1 3/2021 Neuharth et al.
2021/0172499 A1 6/2021 Nino
2021/0330346 A1 10/2021 Jamous et al.
2022/0218385 A1 7/2022 Hilse et al.

FOREIGN PATENT DOCUMENTS

EP 1520509 A1 4/2005
EP 2011446 A2 7/2009
EP 2108304 A2 10/2009
EP 2508141 A1 10/2012
EP 3053534 A1 8/2016
EP 3132760 A1 2/2017
EP 3192461 A1 7/2017
EP 3222228 A1 9/2017
EP 3226784 B1 9/2020
IE S2009529 A2 4/2012
JP H08509639 A 10/1996
JP H10174689 A 6/1998
JP 2001509685 A 7/2001
WO 9424946 A1 11/1994
WO 9629014 A1 9/1996
WO 9814124 A1 4/1998
WO 0051511 A1 9/2000
WO 0056230 A2 9/2000
WO 2001054595 A1 8/2001
WO 0189393 A1 11/2001
WO 0249518 A2 6/2002
WO 2004080507 A2 9/2004
WO 2008016592 A2 2/2008
WO 2008045376 A2 4/2008

(56) References Cited

FOREIGN PATENT DOCUMENTS

| | | | |
|---|---|---|---|
| WO | 2008098124 | A1 | 8/2008 |
| WO | 2010036227 | A1 | 4/2010 |
| WO | 2010056714 | A1 | 5/2010 |
| WO | 2010089727 | A1 | 8/2010 |
| WO | 2011060192 | A1 | 5/2011 |
| WO | 2011106053 | A1 | 9/2011 |
| WO | 2013158849 | A2 | 10/2013 |
| WO | 2014106847 | A1 | 7/2014 |
| WO | 2016001932 | A1 | 1/2016 |
| WO | 2016144834 | A1 | 9/2016 |
| WO | 2016200811 | A1 | 12/2016 |
| WO | 2017087856 | A1 | 5/2017 |
| WO | 2018156603 | A1 | 8/2018 |
| WO | 2019118522 | A1 | 6/2019 |
| WO | 2019168784 | A1 | 9/2019 |
| WO | 2020055728 | A1 | 3/2020 |
| WO | 2020223433 | A1 | 11/2020 |

OTHER PUBLICATIONS

International Search Report and Written Opinion dated Aug. 20, 2019 for International Application No. PCT/US2019/033748.
International Search Report and Written Opinion dated Oct. 1, 2019 for International Application No. PCT/US2019/038006.
Invitation to Pay Additional Fees dated Sep. 26, 2019 for International Application No. PCT/US2019/037995.
International Search Report and Written Opinion dated Dec. 6, 2019 for International Application No. PCT/US2019/037995.
Invitation to Pay Additional Fees dated Nov. 18, 2019 for International Application No. PCT/US2019/049774.
International Search and Written Opinion dated Sep. 20, 2019 for International Application No. PCT/2019/039312.
International Search Report and Written Opinion dated Jun. 4, 2021 for International Application No. PCT/US2021/017939.
International Search Report and Written opinion dated Mar. 28, 2018 for International Application No. PCT/US2018/013587.
International Search Report and Written Opinion dated Apr. 17, 2019 for International Application No. PCT/US2019/018121.
International Search Report and Written Opinion dated Apr. 26, 2019, for International Application No. PCT/US2019/019404.
“What is a PID Controller: Working & Its Applications, 2013, EL-PRO-CUS, URL:https://www.elprocus.com/the-working-of-a-pid-controller/” 17 pages, (Year:2013).
International Search Report and Written Opinion dated Apr. 26, 2019, for International Application No. PCT/US2019/019631.
International Search Report and Written Opinion dated Apr. 26, 2019, for International Application No. PCT/US2019/0198848.
International Search Report and Written Opinion dated Mar. 30, 2020 for International Application No. PCT/US2020/014062.
International Search Report and Written Opinion dated Jun. 25, 2020 for International Application No. PCT/US2020/012767.
International Search Report and Written Opinion dated Apr. 22, 2020 for International Application No. PCT/US2020/013764.
International Search Report and Written Opinion dated Jun. 24, 2020 for International Application No. PCT/US2020/027079.
International Search Report and Written Opinion dated Sep. 4, 2020 for International Application No. PCT/US2020/038132.
International Search Report and Written Opinion dated Sep. 7, 2020 for International Application No. PCT/US2020/038145.
International Search Report and Written Opinion dated Dec. 8, 2020 for International Application No. PCT/US2020/049999.
Invite to Pay Additional Fees dated Feb. 16, 2021 for International Application No. PCT/US2020/061383.
International Search Report and Written Opinion dated Feb. 22, 2022 for International Application No. PCT/US2021/057279.
International Search Report and Written Opinion dated Jan. 26, 2022 for International Application No. PCT/US2021/056616.
International Search Report and Written Opinion dated Nov. 9, 2022 for International Application No. PCT/US2022/041265.

* cited by examiner

ATHERECTOMY SYSTEM ADAPTED TO ENABLE RETROGRADE ABLATION

CROSS-REFERENCE TO RELATED APPLICATIONS

This application claims the benefit of priority under 35 U.S.C. § 119 of U.S. Provisional Application No. 63/297,953, filed Jan. 10, 2022, the entire disclosure of which is hereby incorporated by reference.

TECHNICAL FIELD

The present disclosure pertains to medical devices, and methods for manufacturing and using medical devices. More particularly, the disclosure is directed to devices and methods for removing occlusive material from a body lumen. Further, the disclosure is directed to an atherectomy device for forming a passageway through an occlusion of a body lumen, such as a blood vessel.

BACKGROUND

A wide variety of medical devices have been developed for medical use, for example, for use in accessing body cavities and interacting with fluids and structures in body cavities. Some of these devices may include guidewires, catheters, pumps, motors, controllers, filters, grinders, needles, valves, and delivery devices and/or systems used for delivering such devices. These devices are manufactured by any one of a variety of different manufacturing methods and may be used according to any one of a variety of methods. Of the known medical devices and methods, each has certain advantages and disadvantages.

SUMMARY

This disclosure provides design, material, manufacturing method, and use alternatives for medical devices. As an example, an atherectomy system is adapted for both anterograde ablation and retrograde ablation. The atherectomy system includes a drive coil and an atherectomy tool that is coupled to the drive coil. The atherectomy tool includes a distal region adapted for anterograde ablation and a proximal region adapted for retrograde ablation. A proximal handle includes an actuation member adapted to be movable in a first direction to urge the atherectomy tool in an anterograde ablation direction and to be movable in a second direction to urge the atherectomy tool in a retrograde ablation direction. The atherectomy system is adapted such that the actuation member provides a similar feedback to a user regardless of whether the atherectomy tool is ablating in the anterograde ablation direction or in the retrograde ablation direction.

Alternatively or additionally, the drive coil may be adapted such that the actuation member provides a similar feedback to a user regardless of whether the atherectomy tool is ablating in the anterograde ablation direction or in the retrograde ablation direction.

Alternatively or additionally, the drive coil may have an axial force-torque ratio that is less than 50 gf/mNm and greater than −50 gf/mNm.

Alternatively or additionally, the drive coil may have a tensile stiffness within a range of 0 to 5 N/mm (gage length of 100 mm) and a compressive stiffness within a range of 0 to 10 N/mm (gage length of 10 mm).

Alternatively or additionally, the drive coil may have a torsional stiffness within a range of 0 to 0.05 mNm/degree (gage length of 200 mm).

Alternatively or additionally, the drive coil may have a bending stiffness that is less than 0.5 N/mm (23 mm span).

Alternatively or additionally, the drive coil may have a torque to failure value that is greater than 1 mNm.

Alternatively or additionally, the drive coil may include a single layer coil, a bi-layer coil, a tri-layer coil, or a quad-layer coil.

Alternatively or additionally, the atherectomy system may further include a drive motor operably coupled with the drive coil.

As another example, an atherectomy system is adapted to enable bidirectional ablation. The atherectomy system includes a proximal handle including an actuation member adapted to be movable in a first direction in order to implement anterograde ablation and to be movable in a second direction in order to implement retrograde ablation. An atherectomy tool includes a distal region adapted for anterograde ablation and a proximal region adapted for retrograde ablation. A drive coil extends between the proximal handle and the atherectomy tool and is adapted to provide predictable feedback via the actuation member regardless of whether the atherectomy tool is implementing retrograde ablation or anterograde ablation.

Alternatively or additionally, the drive coil may have an axial force-torque ratio that is less than 10 gf/mNm and greater than −10 gf/mNm.

Alternatively or additionally, the drive coil may have a tensile stiffness within a range of 0.5 to 2 N/mm (gage length of 100 mm).

Alternatively or additionally, the drive coil may have a compressive stiffness within a range of 3.5 to 5 N/mm (gage length of 10 mm).

Alternatively or additionally, the drive coil may have a torsional stiffness within a range of 0.0004 to 0.002 mNm/degree (gage length of 200 mm).

Alternatively or additionally, the drive coil may have a bending stiffness that is less than 0.1 N/mm (23 mm span).

Alternatively or additionally, the drive coil may have a torque to failure value that is greater than 4 mNm.

As another example, an atherectomy system is adapted to enable bidirectional ablation. The atherectomy system includes a proximal handle including an actuation member adapted to be movable in a first direction to cause the atherectomy burr to move in an anterograde ablation direction and to be movable in a second direction to cause the atherectomy burr to move in a retrograde ablation direction. An atherectomy tool includes a distal region adapted for anterograde ablation and a proximal region adapted for retrograde ablation. A drive coil extends between the proximal handle and the atherectomy tool, and is adapted to provide a force-torque ratio that is between −10 gf/mNm and 10 gf/mNm, a tensile stiffness within a range of 0.5 to 2 N/mm (gage length of 100 mm), and a compressive stiffness within a range of 3.5 to 5 N/mm (gage length of 10 mm).

Alternatively or additionally, the drive coil may have a torsional stiffness within a range of 0.0004 to 0.002 mNm/degree (gage length of 200 mm).

Alternatively or additionally, the drive coil may have a bending stiffness that is less than 0.1 N/mm (23 mm span).

Alternatively or additionally, the drive coil may have a torque to failure value that is greater than 4 mNm.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
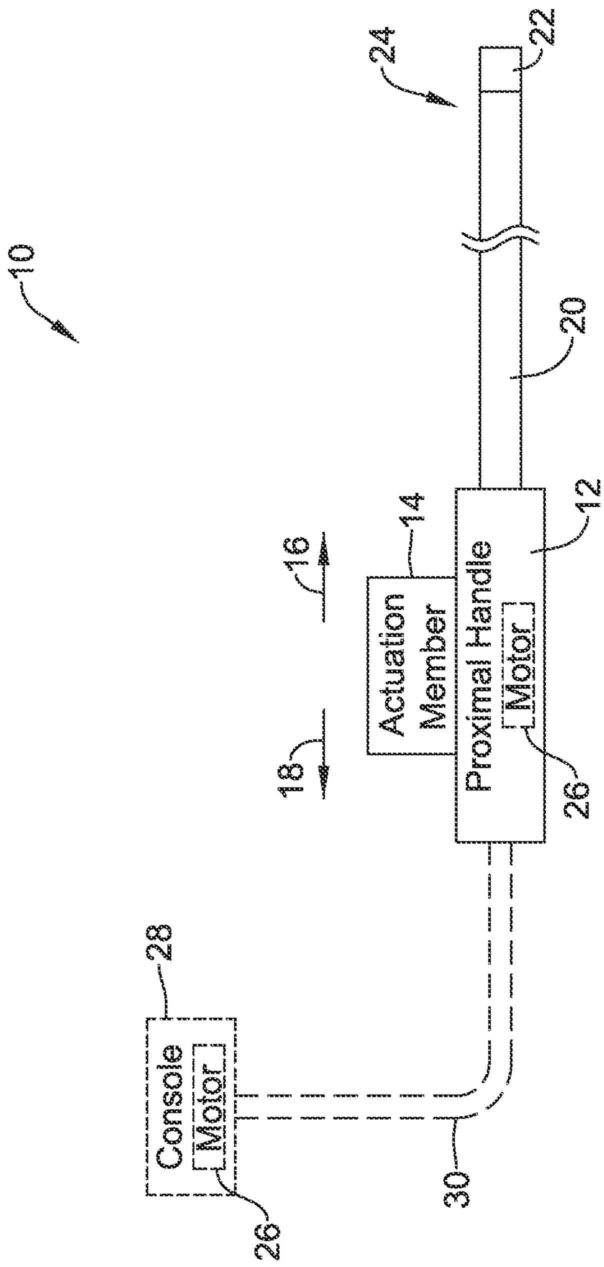
FIG. 1 is a schematic block diagram of an illustrative atherectomy system.

While the disclosure is amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Cardiovascular disease and peripheral arterial disease may arise from accumulation of atheromatous material on the inner walls of vascular lumens, resulting in a condition known as atherosclerosis. Atheromatous and other vascular deposits may restrict blood flow and can cause ischemia in a heart of a patient, vasculature of a patient's legs, a patient's carotid artery, etc. Such ischemia may lead to pain, swelling, wounds that will not heal, amputation, stroke, myocardial infarction, and/or other conditions.

Atheromatous deposits may have widely varying properties, with some deposits being relatively soft and others being fibrous and/or calcified. In the latter case, the deposits may be referred to as plaque. Atherosclerosis occurs naturally as a result of aging, but may also be aggravated by factors such as diet, hypertension, heredity, vascular injury, and the like. Atherosclerosis may be treated in a variety of ways, including drugs, bypass surgery, and/or a variety of catheter-based approaches that may rely on intravascular widening or removal of the atheromatous or other material occluding the blood vessel. Atherectomy is a catheter-based intervention that may be used to treat atherosclerosis.

Atherectomy is an interventional medical procedure performed to restore a flow of blood through a portion of a patient's vasculature that has been blocked by plaque or other material (e.g., blocked by an occlusion). In an atherectomy procedure, a device on an end of a drive shaft that is used to engage and/or remove (e.g., abrade, grind, cut, shave, etc.) plaque or other material from a patient's vessel (e.g., artery or vein). In some cases, the device on an end of the drive shaft may be abrasive and/or may otherwise be configured to remove plaque from a vessel wall or other obstruction in a vessel when the device is rotating and engages the plaque or other obstruction. In some cases, atherectomy involves using an abrasive atherectomy burr that is rotated at high speeds exceeding 100,000 revolutions per minute (RPM) in order to abrade plaque and other hardened materials from within the patient's vessel. Atherectomy burrs may be rotated at speeds exceeding 140,000 RPM, at speeds exceeding 180,000 RPM and even at speeds as high as 220,000 RPM. Atherectomy may include orbital atherectomy in addition to rotational atherectomy.

FIG. 1 is a schematic block diagram of an illustrative atherectomy system 10. The illustrative atherectomy system 10 includes a proximal handle 12 that can be held within a user's hands when operating the atherectomy system 10. In some cases, the proximal handle 12 may instead be adapted to be fixed in space, such as being secured to a table, for example. The atherectomy system 10 includes an actuation member 14 that is slidingly coupled with the proximal handle 12 such that the actuation member 14 can be moved in a first direction relative to the proximal handle 12, indicated by an arrow 16, and in a second direction relative to the proximal handle 12, indicated by an arrow 18.

A drive coil 20 extends distally from the proximal handle 12. An atherectomy tool 22 is secured to a distal end 24 of the drive shaft 20. While not illustrated, the drive shaft 20 includes a lumen that allows the drive shaft 20 to be advanced over a guidewire to reach a treatment site as well as to rotate with respect to the guidewire. It will be appreciated that the drive shaft 20, which is shown schematically, may include additional components. For example, the drive shaft 20 may include an outer sheath (not shown). In some cases, the outer sheath may be adapted to allow the drive shaft 20 to rotate within the outer sheath. In some cases, the outer sheath may be secured such that the drive coil 20 is able to translate relative to the outer sheath. In some cases, the outer sheath may be secured such that outer sheath 20 translates axially as the drive coil 20 translates axially.

In some cases, moving the actuation member 14 in the first direction, indicated by the arrow 16, may result in the drive coil 20 and the atherectomy tool 22 to also move in the direction indicated by the arrow 16. In some instances, moving the actuation member 14 in the first direction, indicated by the arrow 16, may result in the atherectomy tool 22 moving in an anterograde ablation direction. In some cases, moving the actuation member 16 in the second direction, indicated by the arrow 18, may result in the drive coil 20 and the atherectomy tool 22 to also move in the direction indicated by the arrow 18. In some instances, moving the actuation member 14 in the second direction, indicated by the arrow 18, may result in the atherectomy tool moving in a retrograde ablation direction.

The actuation member 14 may take any of a variety of forms. For example, in some cases, the actuation member 14 may simply be a knob that extends out of the proximal handle such that a user can grasp the knob and move it right and left (in the illustrated orientation) in the directions indicated by the arrows 16 and 18. The actuation member 14 may include a knob that slides back and forth, or perhaps a knob that rotates. The actuation member 14 may include a lever that can be moved to indicate a forward direction or a backward direction, for example.

In some cases, particularly if the atherectomy system 10 is configured as a fly-by-wire system without a direct mechanical connection between the actuation member 14 and the drive coil 20, the actuation member 14 may take the form of a joystick or other game controller. In some cases, the actuation member 14 may be a knob that is easily grasped by an operator operating the atherectomy system 10. In some cases, the actuation member 14 may include a touch sensitive controller or even a touch screen. Moving the actuation member 14 back and forth in the directions indicated by arrows 16 and 18 may cause the actuation member 14 to output a request signal to correspondingly move the drive coil 20. Further details regarding atherectomy systems employing fly-by-wire to facilitate ablation in general and retrograde ablation in particular may be found in U.S. Ser. No. 63/257,681, filed Oct. 20, 2021 entitled FLY BY WIRE CONTROL FOR ATHERECTOMY, which reference is incorporated by reference herein.

In some cases, the proximal handle 12 may include a motor 26, such as an electric drive motor, a pneumatic drive motor, a hydraulic drive motor or even a windup drive motor. The motor 26 may be disposed within the proximal handle 12, as shown in phantom. In some cases, the motor 26 may not be disposed within the proximal handle 12, but may instead be remotely located within a console 28, with a flexible drive cable 30 extending from the motor 26 to the proximal handle 12.

In some cases, the drive motor and other components, such as but not limited to a controller that is adapted to regulate operation of the drive motor, may be disposed in a reusable assembly that either remains outside of the sterile field during use, or may be bagged or otherwise sealed for use within the sterile field. In some cases, a reusable assembly may be adapted to be sterilized a plurality of times and thus can be used for more than one patient. In some cases, at least some of the proximal handle 12, the drive shaft 20 and the atherectomy tool 22 may be considered as being part of a single use assembly, that is sterilizable for use with a single patient and then is disposed of. In some cases, the entire atherectomy system 10 may be considered to be adapted for single use. In some cases, the entire atherectomy system 10 may be considered to be adapted for multiple uses.

Figure 2:
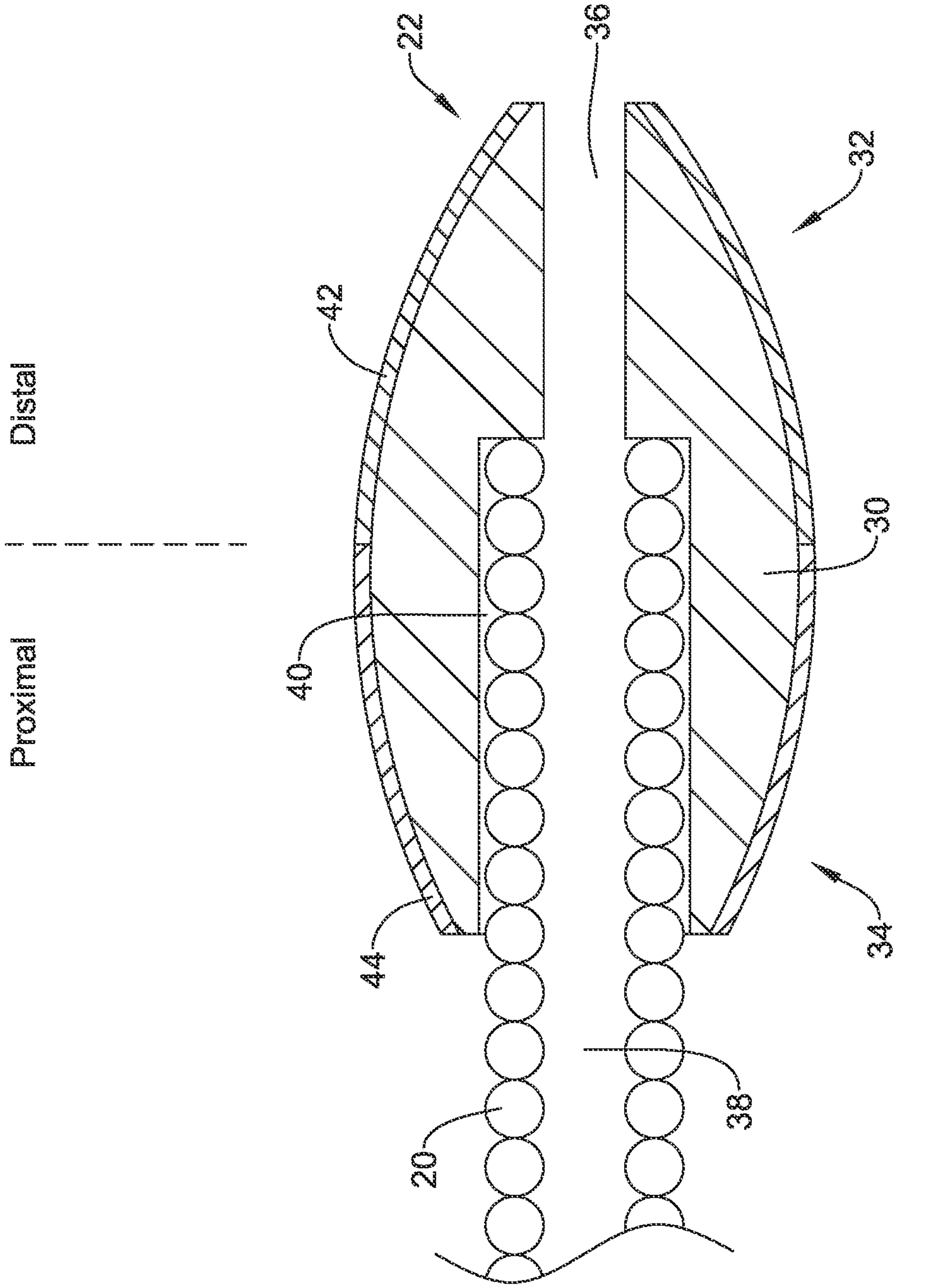
FIG. 2 is a cross-sectional view of an illustrative atherectomy tool usable with the illustrative atherectomy system of FIG. 1.

In order to perform retrograde ablation, and as seen for example in FIG. 2, the atherectomy tool 22 may be adapted for performing both anterograde ablation and retrograde ablation. The atherectomy tool 22 may be seen as having an ovoid body 30 including a distal tapered portion 32 and a proximal tapered portion 34. The atherectomy tool 22 includes a lumen 36 that aligns with a corresponding lumen 38 extending through the drive shaft 20 in order to accommodate a guidewire (not shown). The atherectomy tool 22 includes a void 40 that is adapted to accommodate the drive shaft 20 and to secure the atherectomy tool 22 relative to the drive shaft 20. The atherectomy tool 22 may be adhesively secured, for example, or may be welded or soldered into place.

The distal tapered portion 32 may be considered as being adapted to perform anterograde ablation while the proximal tapered portion 34 may be considered as being adapted to perform retrograde ablation. In some cases, one or both of the distal tapered portion 32 and the proximal tapered portion 34 may include a sharp cutting surface. In some cases, as shown, an abrasive material 42, such as but not limited to diamonds, may be disposed over the distal tapered portion 32. An abrasive material 44, such as but not limited to diamonds, may be disposed over the proximal tapered portion 34. Accordingly, the atherectomy tool 22 may be considered as being adapted for both anterograde ablation and retrograde ablation.

In some cases, the drive shaft 20 is a coil spring. It will be appreciated that a coil spring may have a first set of properties when under compression, such as when the drive shaft 20 is being advanced distally and the atherectomy tool 22 has reached an obstacle, and may have a second set of properties that are different from the first set of properties when under tension, such as when the drive shaft 20 is being withdrawn proximally and the atherectomy tool 22 has reached an obstacle. In some cases, while the drive shaft 20 is intended to rotate in a particular rotational direction when being used to drive the atherectomy tool 22, instances of excessive torque may cause the atherectomy system 10 to behave differently. For example, a controller regulating operation of the proximal handle 12 may stop the drive shaft 20 and may briefly reverse its rotational direction. It will be appreciated that this may cause the drive shaft 20 to alternate between winding, when driven in its primary direction, and unwinding, when either driven in a rotational direction opposite its primary direction or allowed to unwind on its own. It will be appreciated that the feel of the atherectomy system 10, as manifested in the force the user feels when trying to adjust the actuation member 14, may not be consistent depending on what the drive shaft 20 is doing.

In some cases, the atherectomy system 10 may provide a particular feedback to the user when the user is using the atherectomy system 10 to ablate in an anterograde direction, meaning advancing the atherectomy tool 22 in a distal direction into a lesion to be removed or reduced. In some cases, the feedback provided to the user during ablation in an anterograde direction provides predictability, i.e., the user learns to recognize how the feedback the user is receiving via the force the user is applying to the actuation member 14 translates into what the drive shaft 20 is doing. The user learns that a particular application of force via the actuation member 14 means that the atherectomy tool 22 moves a particular distance with a particular force at the lesion, for example. The feedback when ablating in the anterograde direction may be considered as largely being linear, intuitive and predictable.

However, in some cases there may be a desire to also be able to ablate in a retrograde direction, i.e., while moving the atherectomy tool 22 in a proximal direction. This may come about if the user applies too much force, and the atherectomy tool 22 pops through the lesion and ends up distal of the lesion. This is referred to as "watermelon seeding" the atherectomy tool 22. Alternatively or additionally, once a lesion is removed or reduced while ablating in an anterograde direction, the atherectomy tool 22 may be translated distal to the lesion, such that on translation in the proximal direction, the atherectomy tool 22 is able to ablate in the retrograde direction. This is known as "polishing" the lesion. Ablation in both the anterograde direction and the retrograde direction can be advantageous relative to polishing solely in the anterograde direction. In some instances, ablating in a retrograde direction may provide the user with feedback that is less predictable and less "linear". Accordingly, there is a risk of providing too much force, which can cause potential tissue damage or even cause the atherectomy tool 22 to become stuck and in some instances occlude blood flow.

In some cases, the proximal handle 12 may be adapted to customize the feedback provided to the user, in order to make the feedback more consistent regardless of whether ablating in the anterograde ablation direction or ablating in the retrograde ablation direction. Feedback may be considered as including any of a variety of different feedback, and may include one or more of audible feedback, tactile feedback. In some cases, feedback may include mechanical feedback. In some instances, feedback may include vibrational feedback. These are just examples, and are not intended to be limiting. Further details regarding atherectomy systems employing customizable feedback when performing ablation in general and retrograde ablation in particular may be found in U.S. Ser. No. 63/237,679, filed Aug. 27, 2021 entitled ATHERECTOMY SYSTEM WITH ANTEROGRADE AND RETROGRADE ABLATION, which reference is incorporated by reference herein.

Figure 3A:
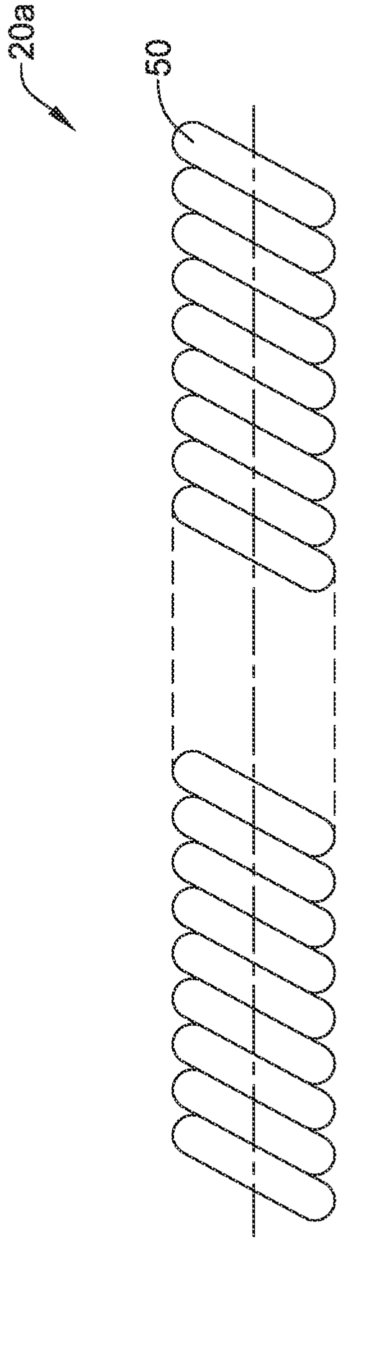
FIG. 3A is a schematic view of an illustrative single layer drive coil.
Figure 3B:
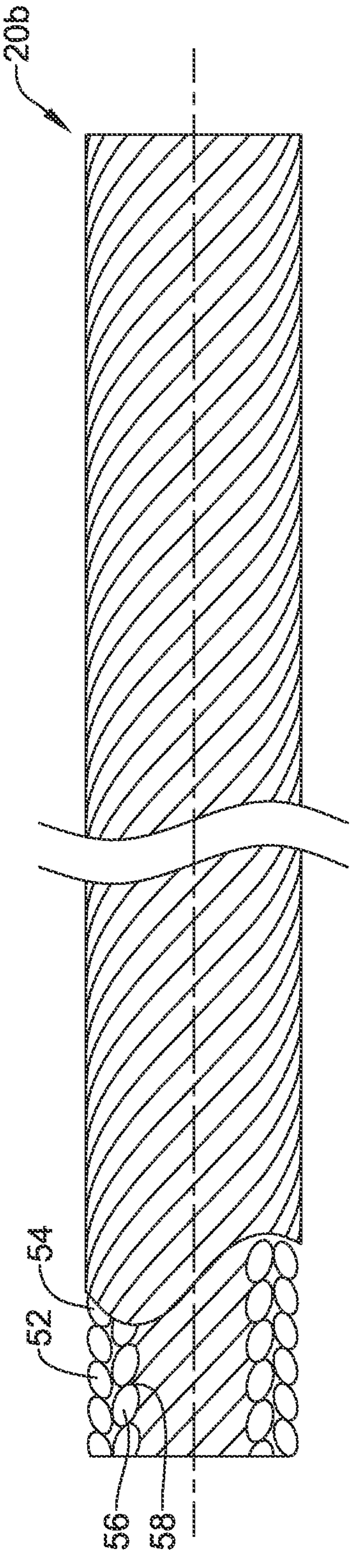
FIG. 3B is a schematic view of an illustrative bi-layer drive coil.

In some cases, the drive coil 20 itself may be adapted to perform well both during anterograde ablation and retrograde ablation. The drive coil 20 may be formed as a single layer coil, a bi-layer coil, a tri-layer coil or even a quad-layer coil, for example. FIG. 3A is a schematic view of a single layer drive coil 20*a* in which one or more filars 50 wound together in a helical direction. FIG. 3B is a schematic view of a bi-layer drive coil 20*b* that includes one or more filars 52 wound together to form an outer layer 54 and one or more filars 56 that are wound together to form an inner layer 58. In some cases, the one or more filars 52 forming the outer layer 54 may be wound in a first helical direction and the one or more filars 56 forming the inner layer 58 may be wound in a second helical direction that may be the same as the first helical direction or that may be opposite the first helical direction.

Figure 3C:
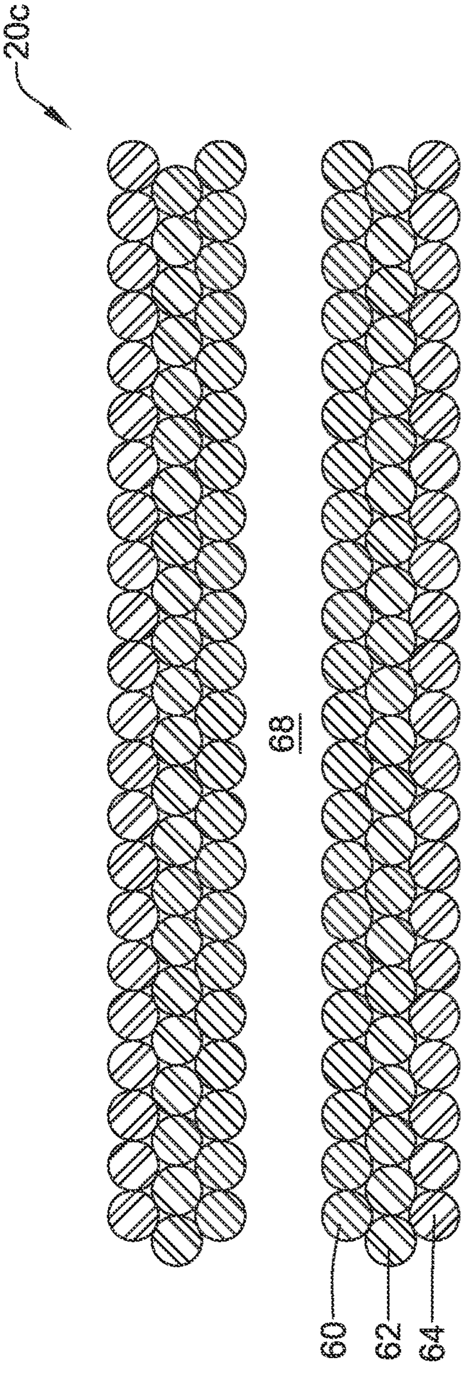
FIG. 3C is a schematic cross-sectional view of an illustrative tri-layer drive coil.
Figure 3D:
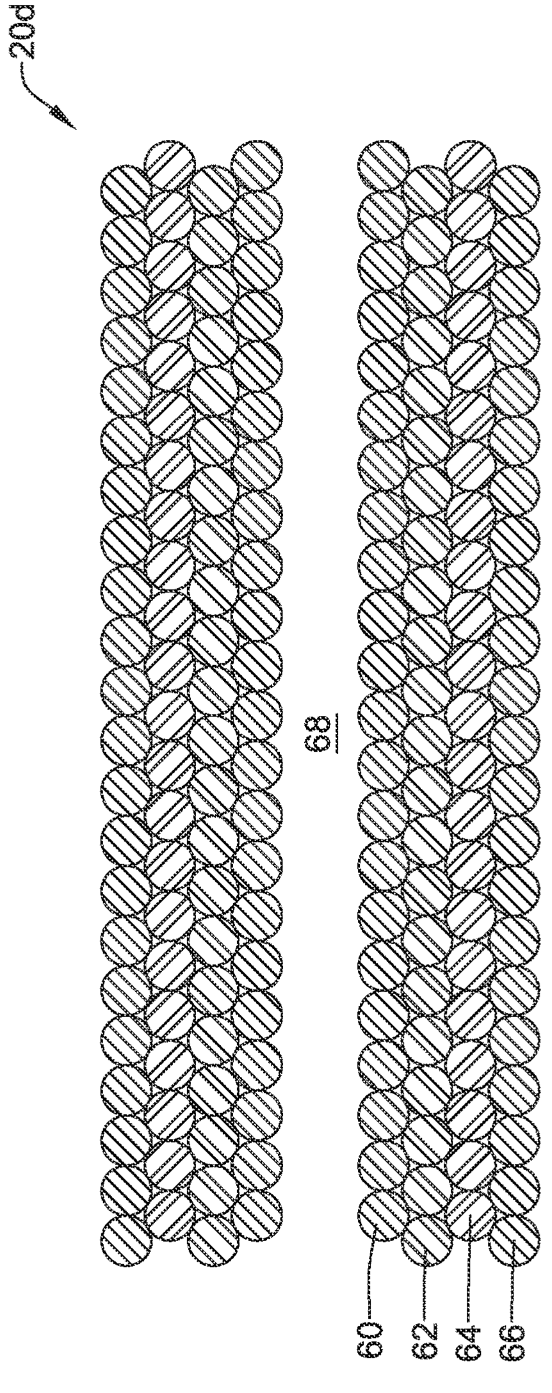
FIG. 3D is a schematic cross-sectional view of an illustrative quad-layer drive coil.

FIG. 3C is a schematic cross-sectional view of a tri-layer drive coil 20*c* that includes a first layer 60, a second layer 62 and a third layer 64. FIG. 3D is a schematic cross-sectional view of a quad-layer drive coil 20*d* that includes the first layer 60, the second layer 62, the third layer 64 and adds a fourth layer 66. The first layer 60 defines a lumen 68 that extends through the drive coil 20*c* and the drive coil 20*d*.

It will be appreciated that atherectomy systems can come in different sizes, using different size sheathes, different size guidewires, and the like. The designs tested herein may be considered as having particular outside diameter requirements, including an OD that is between 0.60 mm and 1.2 mm. Each of these drive coils, depending on OD, can pass a guidewire having a nominal diameter of 0.229 mm to 0.356 mm. While drive coils may be formed of a variety of different materials, in some cases the drive coils are formed of 304V stainless steel. In some cases, the drive coils may be formed of a shape memory alloy of nickel and titanium.

It will be appreciated that in each of the drive coils 20*a*, 20*b*, 20*c* and 20*d*, the number of filars per layer may vary in order to provide a predictable user feedback. The winding direction of each layer may be the same or different. Some of the filars may be wound in a clockwise direction while others are wound in a counter-clockwise direction, for example. Some of the filars may have a round cross-sectional shape. Some of the filars may have a flattened or ovoid cross-sectional shape. Some of the filars may have a square or rectangular cross-sectional shape. Some of the filars may have a three-sided shape, or a five-sided shape, or a six or more-sided shape, for example.

The individual layers may be bare, or may have an intermediate layer that separates the individual layers in order to tailor predictable user feedback while maintaining safety profiles. In some cases, an intermediate layer (if present) may provide lubrication between adjacent layers, allowing relative movement therebetween. In some instances, an intermediate layer (if present) may actually increase friction between adjacent layers, thereby restricting relative movement therebetween.

Each layer may be wound at a particular pitch. In some cases, each layer may be swagged before the subsequent layer. In some instances, the final layer may be swagged in order to customize the properties of the drive coil 20.

It has been discovered through experimentation that a particular combination of performance parameters provides for a drive coil 20 that performs well during anterograde ablation and retrograde ablation as well as providing consistent or expected feedback to the user during both anterograde ablation and retrograde ablation.

An important property is axial or longitudinal force-torque ratio, which can be defined as axial force divided by torque. Put another way, the axial force-torque ratio may be considered as being the slope of a torque versus axial force line. The axial force-torque ratio may be measured using an Instron model 5944, for example. One end of a test coil is held steady while the other end of the test coil is rotated. The resulting torque and axial force values are measured. During testing, the test coils were supported by a 0.04 inch ID (inner diameter) tube, although other sizes are also contemplated. A positive value is tensile, meaning that the coil tries to shorten when subjected to a torque, while a negative value is compressive, meaning that the coil tries to lengthen when subjected to a torque. The shortening and lengthening of the coil generates axial forces. In some cases, a desired axial force-torque ratio is less than 50 gf/mNm (gram force per milli Newton-meters) and greater than −50 gf/mNm. In some cases, a desired axial force-torque ratio is less than 25 gf/mNm and greater than −25 gf/mNm. In some cases, a desired axial force-torque ratio is less than 10 gf/mNm and greater than −10 gf/mNm.

In some cases, it can be useful to consider the axial force-torque ratio in combination with compressive stiffness and tensile stiffness. Compressive stiffness is a relevant parameter for anterograde ablation in which the atherectomy tool 22 is being pushed into contact with a lesion. Tensile stiffness is a relevant parameter for retrograde ablation in which the atherectomy tool 22 is being pulled back into contact with the lesion. In some cases, the forces being applied to the atherectomy tool 22 is a summation of the axial force-torque, the compressive stiffness and/or the tensile stiffness. During anterograde ablation, the primary parameter responsible for providing the user with a predictable indication of the applied force is the compressive stiffness, such that when combined with a positive axial force-torque ratio, the user continues to feel a predictable indication of the applied force. The magnitude of the positive axial force-torque ratio in summation with the compressive stiffness determines the sensitivity, or "springiness" the user feels through the actuation member 14 to the atherectomy tool 22 during anterograde ablation. A negative axial force-torque ratio provides the user with a non-intuitive, non-predictable indication of the applied force during anterograde ablation.

During retrograde ablation, a summation of the tensile stiffness and the axial force-torque provides an indication of the applied force. The magnitude and direction of the axial force-torque ratio in summation with the tensile stiffness can dramatically change the force felt at the lesion by the atherectomy tool 22 relative to the force applied at the actuation member 14 when treating a lesion in retrograde compared to anterograde. A large positive axial force-torque ratio provides the user non-intuitive non-predictable indication of the applied force, such that the lesion feels significantly more force than the user is applying to the actuation member 14 when ablating in retrograde. A negative axial force-torque provides the user a predictable indication of the applied force in retrograde ablation, at the expense of predictable feel in the anterograde ablation direction. The axial force-torque ratio magnitude and direction should be balanced with the summation of the compressive stiffness and or tensile stiffness when treating in anterograde and retrograde to provide the user a predictable and intuitive indication of the applied force in both anterograde and retrograde ablation.

In some cases, a desired compressive stiffness is within a range of 0 to 10 N/mm (Newtons per millimeter), measured over a gage length of 10 mm. In some cases, a desired compressive stiffness is within a range of 3.5 to 5 N/mm, measured over a gage length of 10 mm. In some cases, a desired tensile stiffness is within a range of 0 to 5 N/mm, measured over a gage length of 100 mm. In some cases, a desired tensile stiffness is within a range of 0.5 to 2 N/mm, measured over a gage length of 100 mm. These values are optimized for anterograde ablation, as that is the primary treatment direction until the lesion has been reduced sufficiently to pass the atherectomy tool 22 through the lesion before "polishing" the lesion can occur.

Torsional stiffness is an important property that affects dynamic torque transfer between the motor 26 and the atherectomy tool 22 and needs to remain within a controlled range to protect the integrity of the system and to prevent excessive torque from being delivered to the vessel. Torsional stiffness can also be measured using the Instron model 5944. In some cases, a desired range for torsional stiffness is in the range of 0 to 0.05 mNm/degree (milli Newton-meter per degree), over a gage length of 200 mm. In some cases, a desired range for torsional stiffness is in the range of 0.0004 to 0.002 mNm/degree, over a gage length of 200 mm.

Bending stiffness is an important property that in some cases can be overshadowed by the guidewire used in combination with the drive coil 20 as well as any sheath extending over the drive coil 20, as the guidewire and the sheath may commonly have a bending stiffness that is much higher than that of the drive coil 20. For example, the sheath may have a bending stiffness that is ten or twenty or even more times that the bending stiffness of the drive coil 20. Larger diameter sections of the guidewire may have a bending stiffness that is five or six times that of the bending stiffness of the drive coil 20. Nevertheless, it is desired that the drive coil 20 have a bending stiffness (measured by a three point bend test over a span of 23 mm and a strain rate of 0.1 mm/(mm*min) that is less than 0.5 N/mm. In some cases, the drive coil 20 may have a bending stiffness that is less than 0.1 N/mm, measured over a 23 mm span.

Torque to failure is an important property in ascertaining stability of the drive coil 20 against failure during use, and particularly against failure in the event that the atherectomy tool 22 stops dynamically within a lesion during ablation, such that the drive coil remains intact for subsequent treatment. In some cases, the drive coil 20 has a torque to failure that is greater than 1 mNm (milli Newton-meter). In some cases, the drive coil 20 may have a torque to failure that is greater than 4 mNm.

EXPERIMENTAL SECTION

A number of drive coils were manufactured and tested. Table One below provides a listing of each drive coil and details regarding the construction of each drive coil.

TABLE ONE

| Design # | Inner Filar Count | Outer Filar Count | Inner Filar Diameter (mm) | Outer Filar Diameter (mm) | Inner Filar Winding Direction | Outer Filar Winding Direction |
|---|---|---|---|---|---|---|
| 1 | 3 | — | 0.15 | — | Left (S) | — |
| 2 | 4 | — | 0.15 | — | Left (S) | — |
| 3 | 6 | — | 0.15 | — | Left (S) | — |
| 4 | 6 | | 0.12 | — | Left (S) | — |
| 5 | 12 | 18 | 0.08 | 0.07 | Right (Z) | Left (S) |
| 6 | 12 | 18 | 0.08 | 0.07 | Left (S) | Right (Z) |
| 7 | 10 | 16 | 0.08 | 0.07 | Left (S) | Right (Z) |
| 8 | 8 | 14 | 0.08 | 0.07 | Left (S) | Right (Z) |
| 9 | 6 | 8 | 0.08 | 0.07 | Left (S) | Right (Z) |
| 10 | 8 | 10 | 0.07 | 0.08 | Right (Z) | Right (Z) |
| 11 | 6 | 8 | 0.07 | 0.08 | Right (Z) | Right (Z) |
| 12 | 8 | 10 | 0.07 | 0.08 | Left (S) | Left (S) |
| 13 | 6 | 8 | 0.07 | 0.08 | Left (S) | Left (S) |
| Control | 3 | — | 0.15 | — | Left (S) | — |

Table Two below provides experimental results for the drive coils that were referenced in Table One.

| Design # | Torsional Stiffness CCW (mNm/deg) | Torque to Failure CCW (mNm) | Force-Torque Ratio CCW (gf/mNm) | Retrograde Ablation | Durability |
|---|---|---|---|---|---|
| 1 | 0.00037 | 1.9 | DNA* | FAIL | DNA |
| 2 | 0.00065 | 2.5 | DNA | FAIL | DNA |
| 3 | 0.0014 | 2.2 | DNA | FAIL | DNA |
| 4 | 0.00046 | 1.0 | DNA | FAIL | DNA |
| 5 | 0.00051 | 6.2 | DNA | FAIL | DNA |
| 6 | 0.034 | 15.6 | 12 | PASS | FAIL |
| 7 | 0.033 | 9.9 | 11 | PASS | FAIL |
| 8 | 0.027 | 6.5 | 0 | PASS | Some pass |
| 9 | 0.0067 | 2.0 | 20 | DNA | DNA |
| 10 | 0.0033 | 4.0 | 90 | DNA | DNA |
| 11 | 0.0023 | 2.3 | 89 | DNA | DNA |
| 12 | 0.00020 | 2.0 | 31 | DNA | DNA |
| 13 | 0.00013 | 1.5 | 16 | PASS | Damage during ablation test |
| Control | 0.00037 | 3.7 | 32 | FAIL | PASS |

-continued

| Design # | Torsional Stiffness CCW (mNm/deg) | Torque to Failure CCW (mNm) | Force-Torque Ratio CCW (gf/mNm) | Retro-grade Ablation | Durability |
|---|---|---|---|---|---|

*DNA represents Did Not Assess

Retrograde ablation was tested by placing a drive coil including an atherectomy burr on a distal end thereof between two halves of a clamshell lesion surrogate. A user attempted to ablate the clamshell lesion in a retrograde direction. The user may move the drive coil back and forth, in order to move the atherectomy burr repeatedly into and out of contact with the clamshell lesion. A passing result occurs if the user can ablate without the system stalling.

Figure 4:
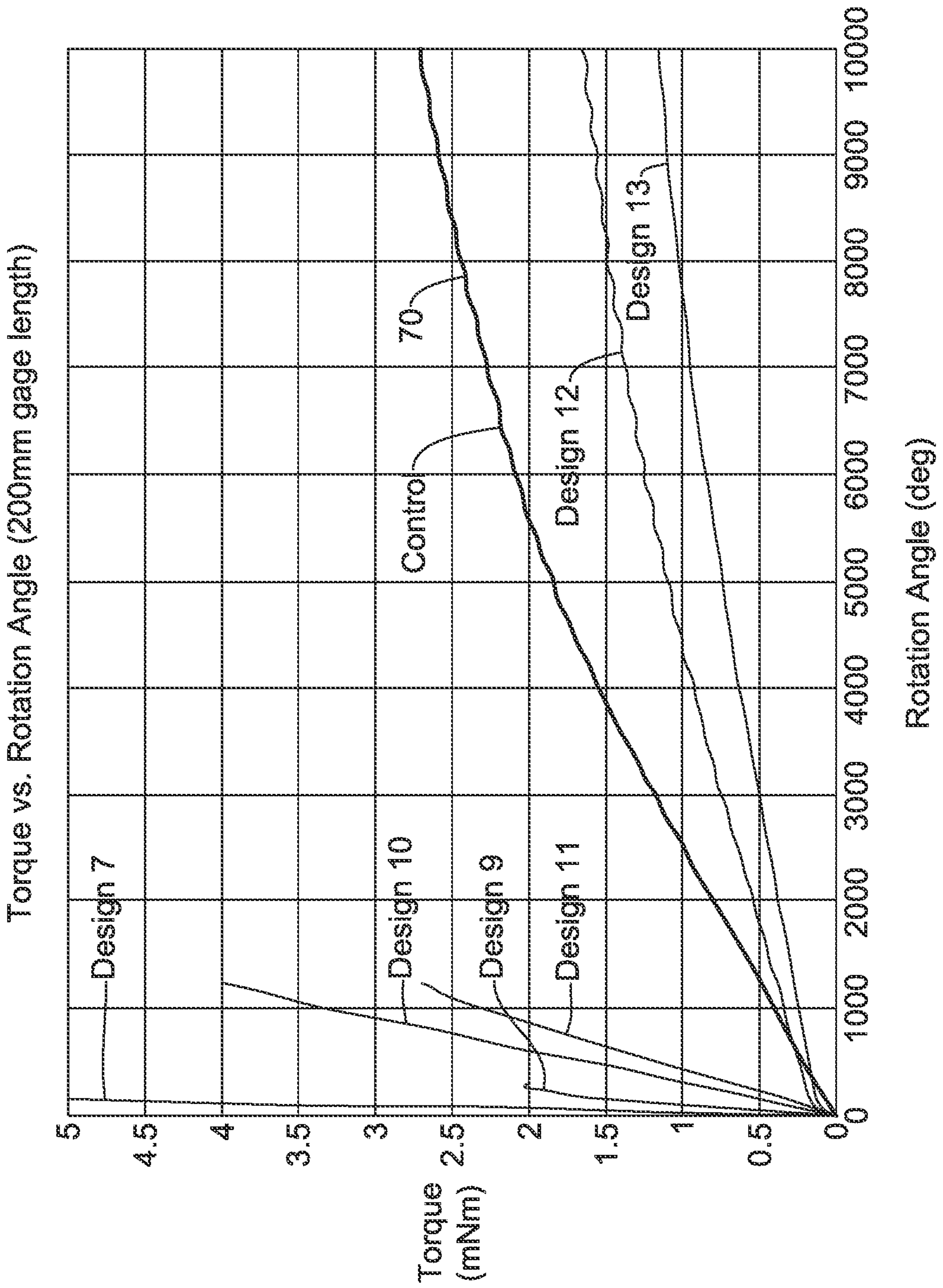
FIG. 4 is a graph showing experimental data.

FIG. 4 is a graph of torque versus rotation angle, showing torque (in milliNewton-meters) plotted on the Y axis and rotation angle (in degrees) plotted on the X axis, measured with a 200 mm gage length. As can be seen, a control, representing an available drive coil, is represented as a graph line 70. Several tested drive coils were substantially more stiff than the control represented by the graph line 70. Two of the tested drive coils were less stiff than the control represented by the graph line 70. In particular, the drive coil design 12 and design 13 had, for a given rotation angle, a lower torque value in comparison with the control represented by the graph line 70.

Figure 5:
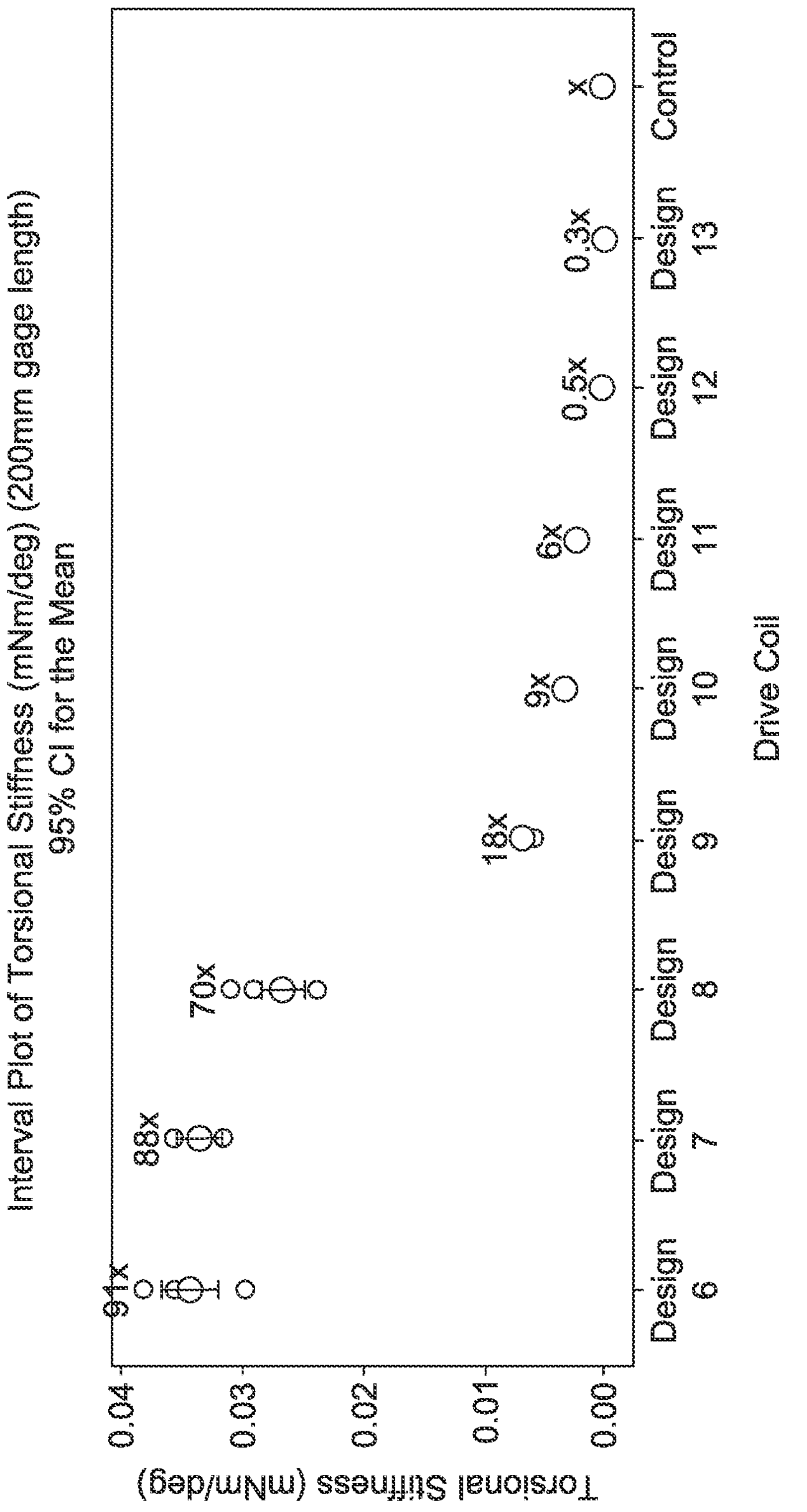
FIG. 5 is a graph showing experimental data.

FIG. 5 is a graph showing torsional stiffness data for each of the tested coil designs, measured with a 200 mm gage length. The data has been normalized by comparing to the control. As can be seen, the control (far right side of the graph) has a torsional stiffness set equal to x. The other tested coil designs are thus compared to x. The coil design 13, for example, has a torsional stiffness that is 0.3 times that of the control. The coil design 9, for example, has a torsional stiffness that is 18 times that of the control. The coil design 6, for example, has a torsional stiffness that is 91 times that of the control.

Figure 6:
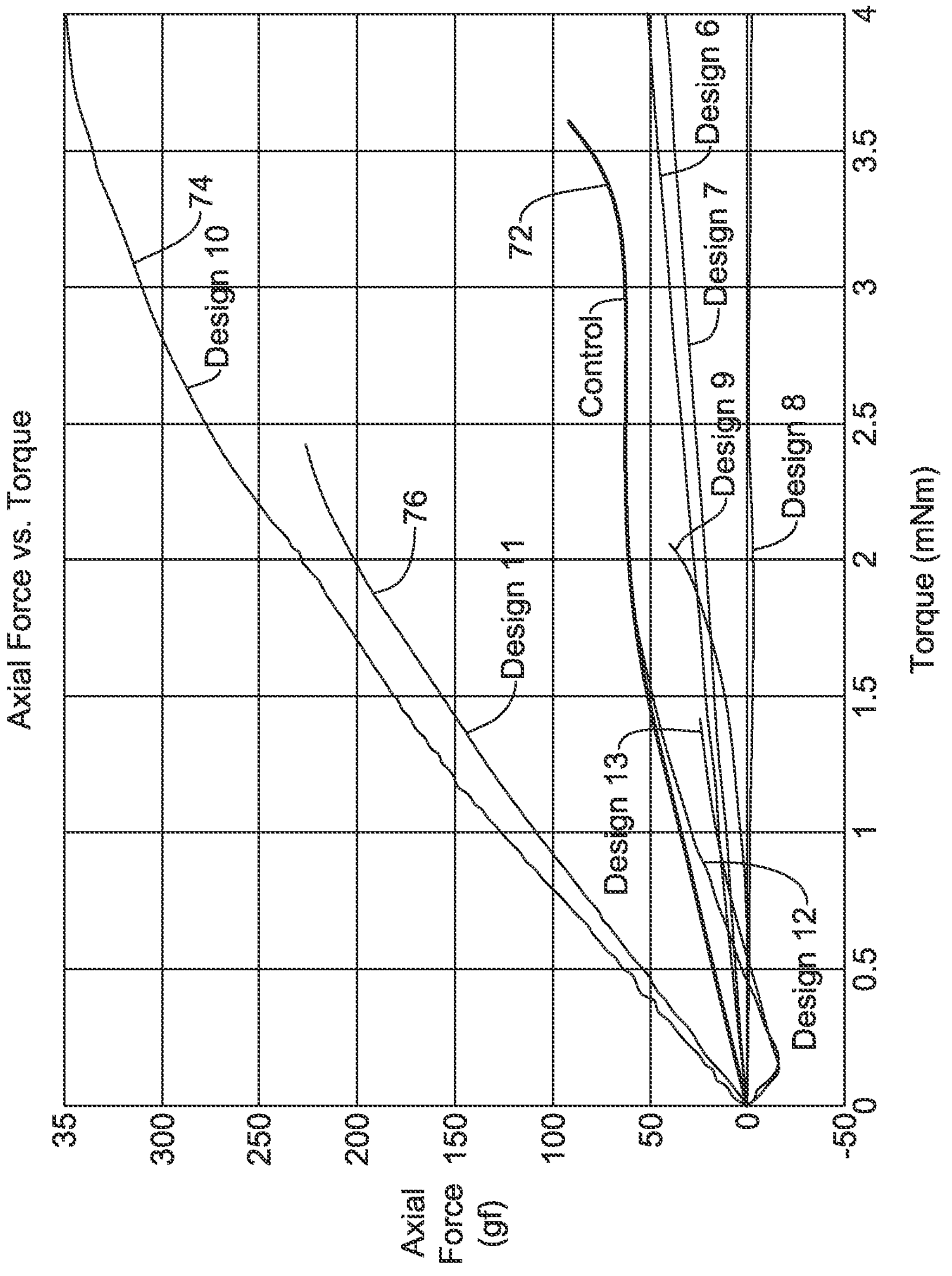
FIG. 6 is a graph showing experimental data.

FIG. 6 is a graph showing axial force plotted on the Y axis and torque plotted on the X axis. A graph line 72 represents the control. As can be seen, several coil designs, such as the design 10, represented by a graph line 74, and design 11, represented by a graph line 76, have force-torque curves that are well above the control, as represented by the graph line 72. The other coil designs all have force-torque curves that are below the control, as represented by the graph line 72. While these force-torque curves are largely positive, indicating shortening, several can be seen as briefly being negative, indicating lengthening.

Figure 7:
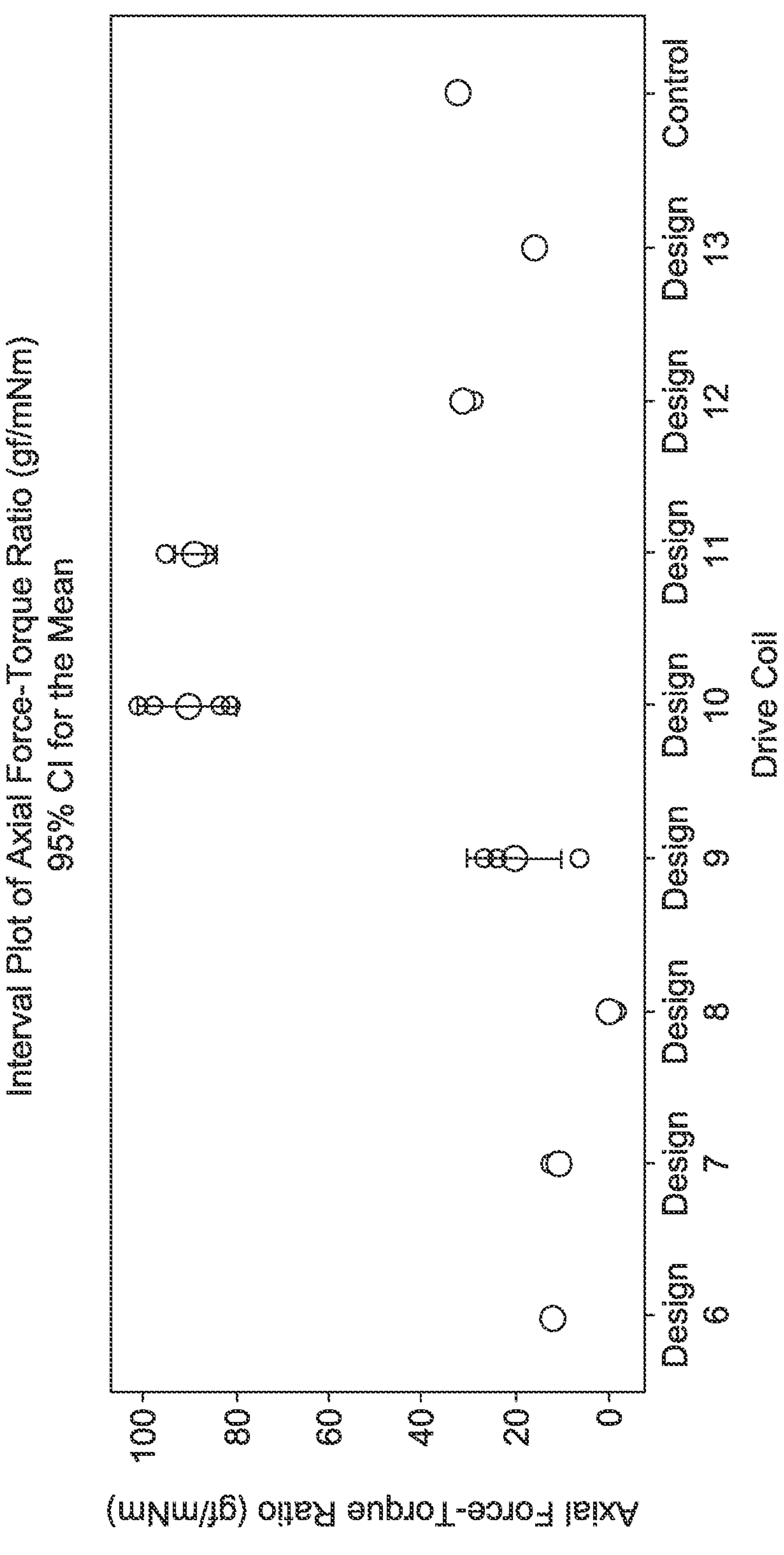
FIG. 7 is a graph showing experimental data.

FIG. 7 is a graph showing force-torque data representing a linear slope average of the data shown in FIG. 6. As with FIG. 5, the data has been normalized relative to the control coil design. In this case, two of the coil designs, design 10 and design 11, have force-torque values that are higher than the control, while the remaining coil designs all have force-torque values that are less than that of the control.

Figure 8:
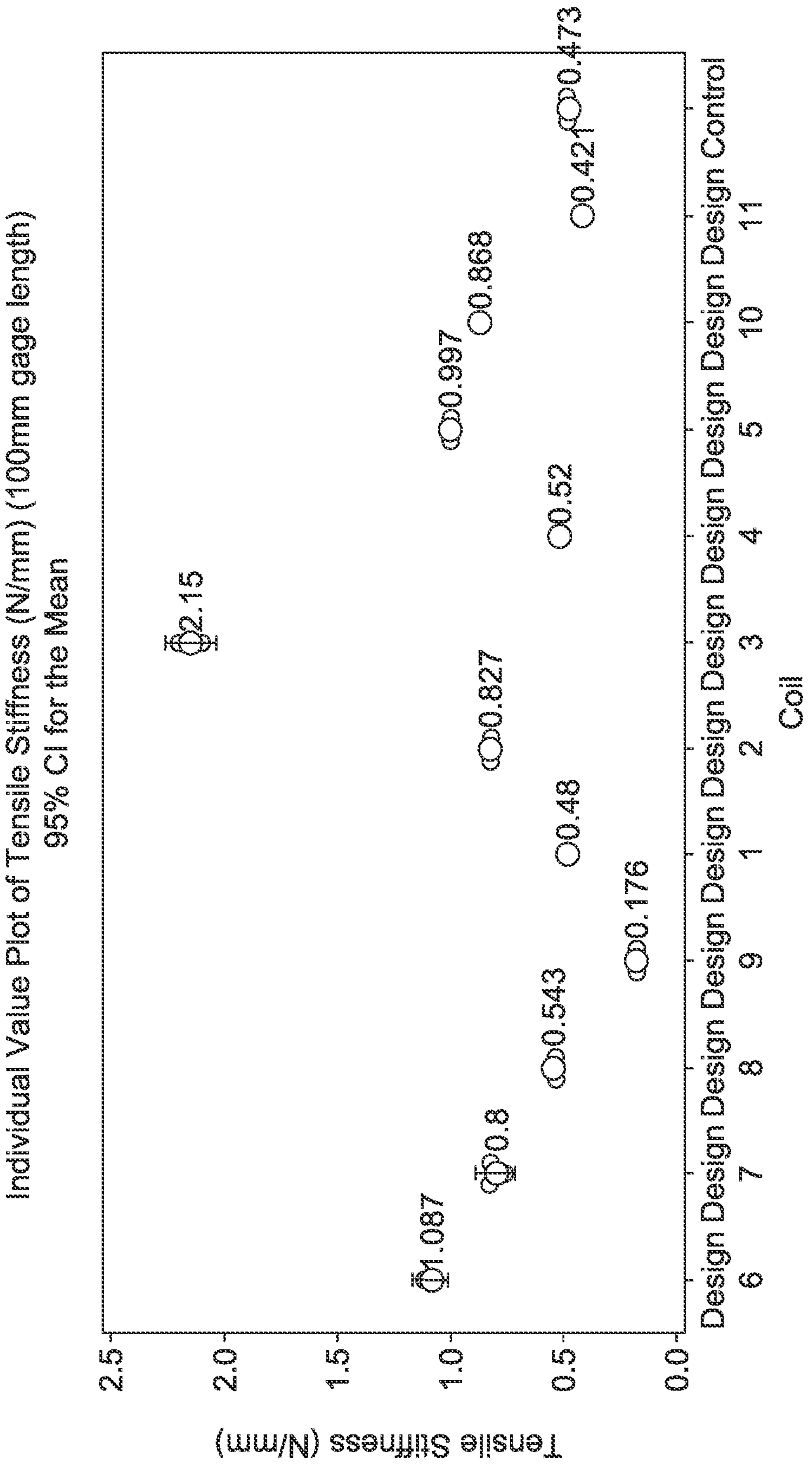
FIG. 8 is a graph showing experimental data.

FIG. 8 is a graph showing tensile stiffness plotted for each of the tested coil designs, measured with a 100 mm gage length. Tensile stiffness, which measures a response to pulling on the coil, is a relevant parameter for evaluating retrograde ablation. It can be seen that the designs tested so far have a tensile stiffness (measured over a 100 mm gage length) that ranges from 0.4 to 4.5 times that of the control, seen at the far right of the graph.

Figure 9:
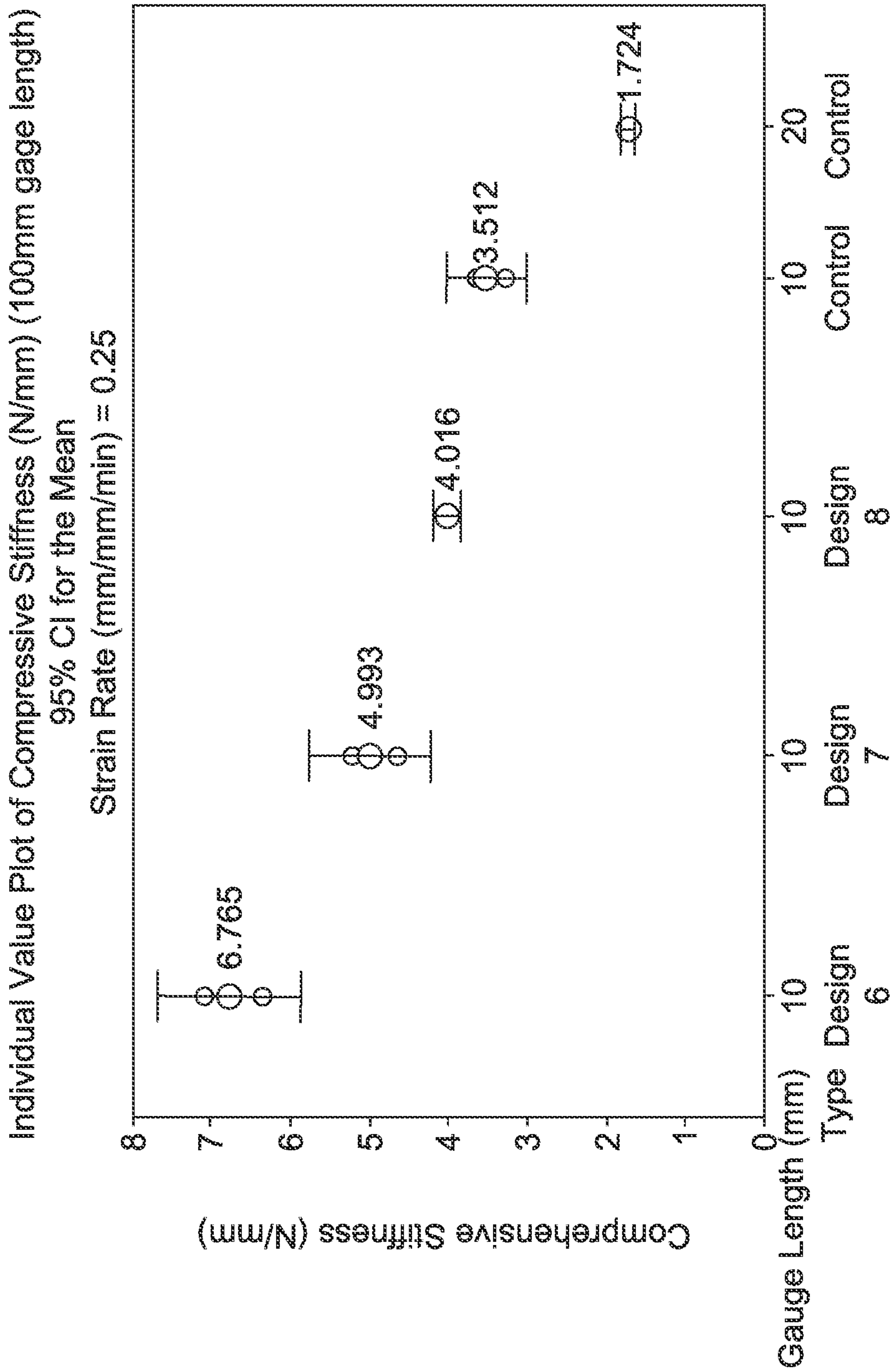
FIG. 9 is a graph showing experimental data.

FIG. 9 is a graph showing compressive stiffness plotted for several of the tested coil designs. Compressive stiffness, which measures a response to pushing on the coil, is a relevant parameter for evaluating anterograde ablation. Compressive stiffness was tested using a 10 mm gage length and a displacement speed of 2.5 mm/min.

Figure 10:
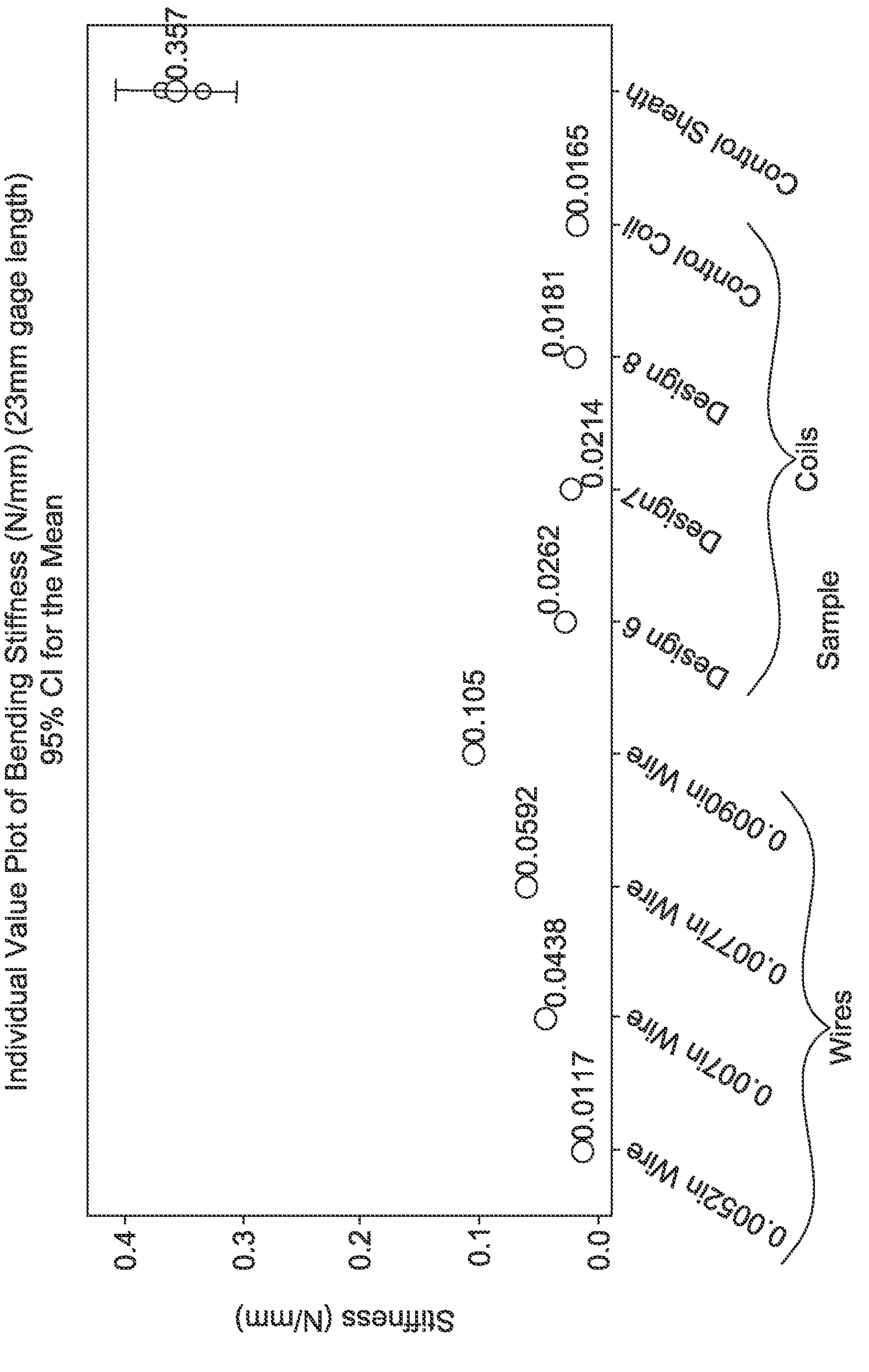
FIG. 10 is a graph showing experimental data.

FIG. 10 is a graph showing bending stiffness plotted for each of the tested coil designs, measured with a 23 mm gage length. As noted, the sheath may have considerably more bending stiffness than the coil itself does. This is evidenced on the right hand side of the graph, where the bending stiffness for the control sheath (far right) is substantially higher than that of the control coil (second to right). FIG. 10 also shows that for the tested coils, the bending stiffness of the coils is less than that of the guidewires plotted on the left side of the graph.

In reviewing the experimental data, it can be seen that the coil designs design 6, design 7, design 8 and design 13 passed the retrograde ablation test. It is believed that this is due to the relatively low values for axial force-torque ratio that these designs possess. Design 6, design 7 and design 8 had torsional stiffness values that were too high. Design 13 has a torque to failure value that was too low.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An atherectomy system adapted for both anterograde ablation and retrograde ablation, the atherectomy system comprising:

a drive coil that is adapted to provide:

- an axial force-torque ratio within a range of −50 gf/mNm to 50 gf/mNm;
- a tensile stiffness within a range of 0 to 5 N/mm (gage length of 100 mm); and
- a compressive stiffness within a range of 0 to 10 N/mm (gage length of 10 mm);

an atherectomy tool coupled to the drive coil, the atherectomy tool including a distal region adapted for anterograde ablation and a proximal region adapted for retrograde ablation; and a proximal handle including an actuation member adapted to be movable in a first direction to urge the atherectomy tool in an anterograde ablation direction and to be movable in a second direction to urge the atherectomy tool in a retrograde ablation direction.

2. The atherectomy system of claim 1, wherein the actuation member provides consistent feedback to a user regardless of whether the atherectomy tool is ablating in the anterograde ablation direction or in the retrograde ablation direction.

3. The atherectomy system of claim 1, wherein the drive coil has a torsional stiffness within a range of 0 to 0.05 mNm/degree (gage length of 200 mm).

4. The atherectomy system of claim 1, wherein the drive coil has a bending stiffness that is less than 0.5 N/mm (23 mm span).

5. The atherectomy system of claim 1, wherein the drive coil has a torque to failure value that is greater than 1 mNm.

6. The atherectomy system of claim 1, wherein the drive coil comprises a single layer coil, a bi-layer coil, a tri-layer coil, or a quad-layer coil.

7. The atherectomy system of claim 1, further comprising a drive motor operably coupled with the drive coil.

8. An atherectomy system adapted to enable bidirectional ablation, the atherectomy system comprising:

a proximal handle including an actuation member adapted to be movable in a first direction in order to implement anterograde ablation and to be movable in a second direction in order to implement retrograde ablation;

an atherectomy tool including a distal region adapted for anterograde ablation and a proximal region adapted for retrograde ablation; and a drive coil extending between the proximal handle and the atherectomy tool, the drive coil adapted to provide consistent feedback via the actuation member regardless of whether the atherectomy tool is implementing retrograde ablation or anterograde ablation;

wherein the drive coil has a tensile stiffness within a range of 0.5 to 2 N/mm (gage length of 100 mm).

9. The atherectomy system of claim 8, wherein the drive coil has an axial force-torque ratio within a range of −10 gf/mNm and 10 gf/mNm.

10. The atherectomy system of claim 8, wherein the drive coil has a compressive stiffness within a range of 3.5 to 5 N/mm (gage length of 10 mm).

11. The atherectomy system of claim 8, wherein the drive coil has a torsional stiffness within a range of 0.0004 to 0.002 mNm/degree (gage length of 200 mm).

12. The atherectomy system of claim 8, wherein the drive coil has a bending stiffness that is less than 0.1 N/mm (23 mm span).

13. The atherectomy system of claim 8, wherein the drive coil has a torque to failure value that is greater than 4 mNm.

14. An atherectomy system adapted to enable bidirectional ablation, the atherectomy system comprising:

a proximal handle including an actuation member adapted to be movable in a first direction to cause an atherectomy burr to move in an anterograde ablation direction and to be movable in a second direction to cause the atherectomy burr to move in a retrograde ablation direction;

the atherectomy burr including a distal region adapted for anterograde ablation and a proximal region adapted for retrograde ablation; and a drive coil extending between the proximal handle and the atherectomy burr, the drive coil adapted to provide:

a force-torque ratio within a range of −10 gf/mNm to 10 gf/mNm;

a tensile stiffness within a range of 0.5 to 2 N/mm (gage length of 100 mm); and a compressive stiffness within a range of 3.5 to 5 N/mm (gage length of 10 mm).

15. The atherectomy system of claim 14, wherein the drive coil has a torsional stiffness within a range of 0.0004 to 0.002 mNm/degree (gage length of 200 mm).

16. The atherectomy system of claim 14, wherein the drive coil has a bending stiffness that is less than 0.1 N/mm (23 mm span).

17. The atherectomy system of claim 14, wherein the drive coil has a torque to failure value that is greater than 4 mNm.

* * * * *